US00PP21456P2

(12) United States Plant Patent
Pieters

(10) Patent No.: US PP21,456 P2
(45) Date of Patent: Nov. 9, 2010

(54) ***CHRYSANTHEMUM* PLANT NAMED 'PPP MABEL 09'**

(50) Latin Name: *Chrysanthemum morifolium*
Varietal Denomination: PPP MABEL 09

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/462,588

(22) Filed: Aug. 5, 2009

(51) Int. Cl.
*A01H 5/00* (2006.01)

(52) U.S. Cl. ..... Plt./291
(58) Field of Classification Search ..... Plt./291, Plt./287
See application file for complete search history.

*Primary Examiner*—Annette H Para
*Assistant Examiner*—Louanne C Krawczewicz Myers
(74) *Attorney, Agent, or Firm*—Mark P. Bourgeois

(57) ABSTRACT

A new and distinct *Chrysanthemum* plant cultivar is disclosed, characterized by large decorative type inflorescences, consistent flowering response to short days, blooming consistently after 49 days of short day length, light pink ray florets, free branching habit, and a consistent natural season flowering habit during the first week of September.

1 Drawing Sheet

Latin name of the genus and species: *Chrysanthemum morifolium.*

Variety denomination: 'PPP MABEL 09'.

BACKGROUND OF THE INVENTION

The new cultivar 'PPP MABEL 09' is a product of a cross between the male parent 'GEDI TWO PAD' (U.S. Plant Pat. No. 14,501) and the female parent 'GEDI TWO CAM' (U.S. Plant Pat. No. 14,472). The new cultivar was discovered and selected by Dirk Pieters in September of 2008 in a greenhouse in Oostnieuwkerke, Belgium.

Asexual reproduction of the new cultivar 'PPP MABEL 09' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP MABEL 09' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP MABEL 09.' These characteristics in combination distinguish 'PPP MABEL 09' as a new and distinct *Chrysanthemum* cultivar:

1. Light pink, decorative-type inflorescences;
2. Consistent natural season flowering habit during the first week of September;
3. Free branching habit; and
4. Consistent flowering response to short days, blooming consistently after 49 days of short day length.

Plants of the new cultivar 'PPP MABEL 09' are similar to plants of the male parent variety, 'Gedi Two Pad' in most horticultural characteristics; however plants of the new cultivar 'PPP MABEL 09' are smaller in both height and plant spread. Also, the new cultivar 'PPP MABEL 09' has a smaller inflorescence diameter. Additionally, the ray florets of 'PPP MABEL 09' are a much lighter pink than the male parent. Finally, the new cultivar blooms one week earlier than the male parent.

Plants of the new cultivar 'PPP MABEL 09' are similar to plants of the female parent variety, 'GEDI TWO CAM' in most horticultural characteristics, however plants of the new cultivar 'PPP MABEL 09' has a smaller plant spread. Finally, the ray florets of the female parent 'GEDI TWO CAM' are dark red compared to the light pink ray florets of the new cultivar.

In comparison to the commercially available variety 'PPP MIL PK05' (U.S. Plant Pat. No. 16,968), 'PPP MABEL 09' is smaller in both height and plant spread. Additionally, the new variety 'PPP MABEL 09' has a smaller inflorescence diameter. Further, the comparable variety 'PPP MIL PK05' has more inflorescences per lateral branch. Finally, 'PPP MABEL 09' naturally blooms two weeks later.

BRIEF DESCRIPTION OF THE PHOTOGRAPH

The accompanying photograph in the drawing illustrates in full color a typical plant of 'PPP MABEL 09' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP MABEL 09' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP MABEL 09.'

Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 20 cm.
Plant spread: Approximately 30 cm.
Growth rate: Moderate.
Branching characteristics: Free branching.
Length of lateral branches: Approximately 15 cm.
*Diameter of lateral branches.*—About 5.0 mm.
*Color of lateral branches.*—Near Yellow Green 147B.
Number of leaves per lateral branch: Approximately 28.
Age of plant described: Approximately 137 days.

FOLIAGE

Leaf:
*Arrangement.*—Alternate single.
*Average length.*—Approximately 4.8 cm.
*Average width.*—Approximately 4.2 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 0.7 cm.
*Color.*—Young foliage upper side: Near Yellow-Green 147A. Young foliage under side: Near Yellow-Green 147B. Mature foliage upper side: Near Yellow-Green 147A. Mature foliage under side: Near Yellow-Green 147B.
*Venation.*—Type: Palmately net. Venation color upper side: Near Green 138B. Venation color under side: Near Green 138B.
Petiole:
*Average length.*—Approximately 1.3 cm.
*Color.*—Near Green 138B.
*Diameter.*—Approximately 0.4 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the first week in September.
*Number of inflorescences per lateral branch.*—Approximately 18.
*Inflorescence diameter.*—Approximately 3.1 cm.
*Inflorescence depth.*—Approximately 1.2 cm.
*Disc diameter.*—Approximately 1.0 cm.
*Receptacle height.*—About 5 mm.
*Receptacle diameter.*—About 4 mm.
*Fragrance.*—None.
*Inflorescence longevity on plant.*—Approximately 25 to 30 days.
*Persistence.*—Persistent.
Ray florets:
*Appearance.*—Matte.
*Texture (both surfaces).*—Smooth.
*Average number of ray florets per inflorescence.*—128.
*Shape.*—Oblanceolate.
*Aspect.*—Flat.
*Margin.*—Entire.
*Apex.*—Obtuse.
*Base.*—Attenuate.
*Length.*—Approximately 1.2 cm.
*Width.*—Approximately 0.3 cm.
*Color.*—Upper surface at first opening: Near Red-Purple 62D. Upper surface at maturity: Near Red-Purple 62C. Upper surface at fading: Near Red-Purple 62D. Under surface at first opening: Near Red-Purple 62D. Under surface at maturity: Near Red-Purple 62D. Under surface at fading: Near Red-Purple 62D.
Disc florets:
*Appearance.*—Shiny.
*Texture.*—Smooth.
*Average number of florets per disc.*—Approximately 15.
*Shape.*—Cylindric.
*Apex.*—Obtuse.
*Average length.*—Approximately 0.3 cm.
*Average width.*—Approximately 0.1 cm.
*Color.*—At first opening: Near Yellow-Green 154B. At maturity: Near Yellow 9A. At fading: Near Yellow 9A.
Peduncle:
*Length.*—At terminal end (shortest): Approximately 3.4 cm. At lateral end (longest): Approximately 6.4 cm.
*Angle to stem.*—Acute.
*Strength.*—Moderate.
*Color.*—Near Green 138A.
*Habit.*—Upright.
*Diameter.*—Approximately 0.2 cm.
*Surface texture.*—Lightly pubescent.
Inflorescence bud:
*Length.*—Approximately 0.4 cm.
*Diameter.*—Approximately 0.6 cm.
*Form.*—Globular.
*Color.*—Near Red-Purple 62C.
Involucral bracts (phyllaries):
*Appearance.*—Matte.
*Texture.*—Lightly pubescent.
*Number.*—Approximately 25.
*Shape.*—Lanceolate.
*Margin.*—Entire.
*Apex.*—Obtuse.
*Length.*—Approximately 0.4 cm.
*Width.*—Approximately 0.3 cm.
*Color.*—Upper side: Near Green 137A. Under side: Near Green 137C.

REPRODUCTIVE ORGANS

Ray florets:
*Number of pistils per floret.*—1.
*Stigma shape.*—2 branched.
*Stigma color.*—Near Yellow 9A.
*Style color.*—Near Green-Yellow 1C.
*Style length.*—Approximately 0.2 cm.
*Stamens.*—Absent.
Disc florets:
*Number of pistils per floret.*—1.
*Stigma shape.*—Cylindric.

*Stigma color.*—Near Yellow 9A.
*Style length.*—Approximately 0.2 cm.
*Style color.*—Near Green-Yellow 1D.
*Number of stamens per floret.*—Approximately 5.
*Anther shape.*—Tubular.
*Anther color.*—Near Yellow 9A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP MABEL 09' as herein illustrated and described.

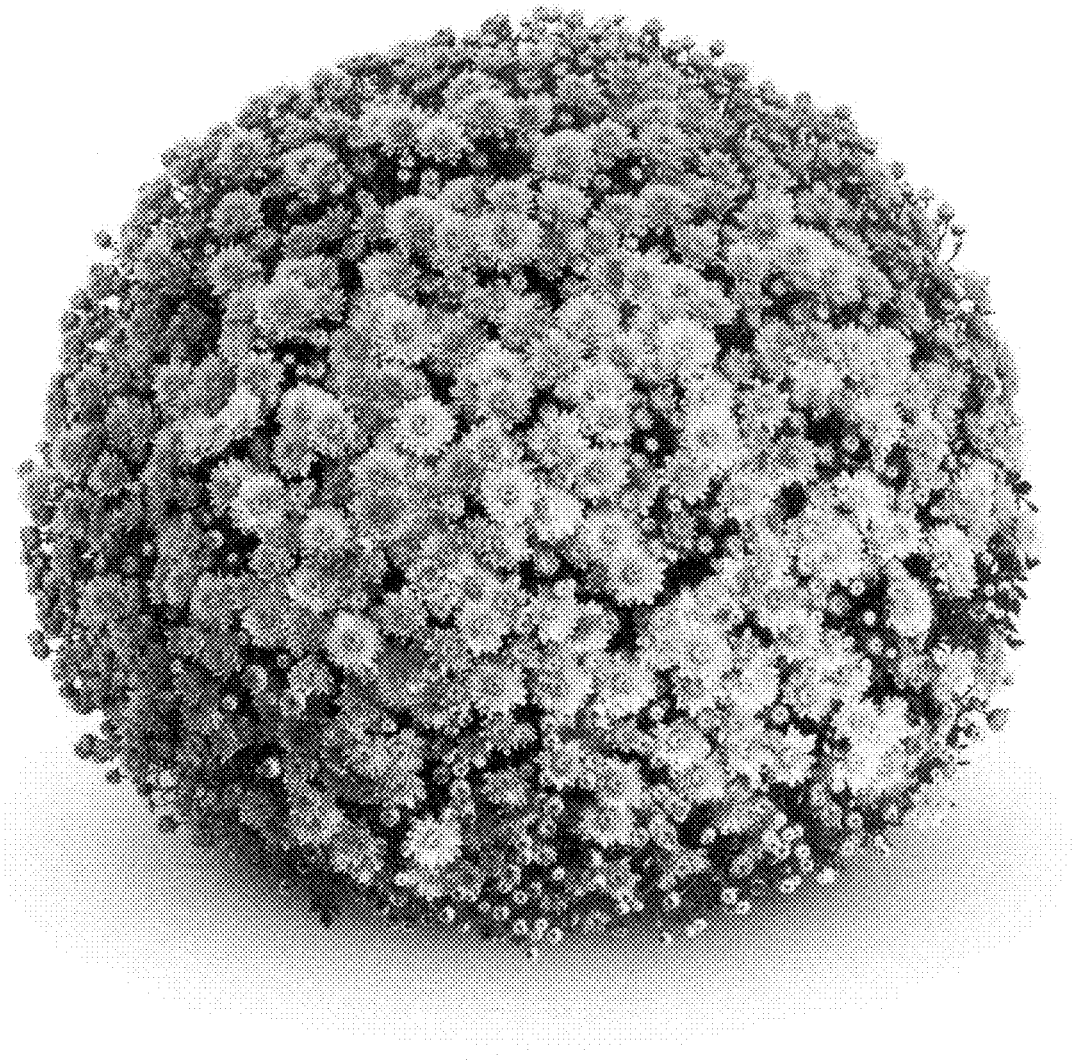

* * * * *